United States Patent [19]

Pigeon

[11] 4,061,968

[45] Dec. 6, 1977

[54] PROCESS OF AND APPARATUS FOR NON-DESTRUCTIVE EDDY CURRENT TESTING INVOLVES THE SUPPRESSION OF DISPLAYED LOBES CORRESPONDING TO FAULT PARAMETERS TO BE ELIMINATED FROM THE DISPLAY

[75] Inventor: Michel Pigeon, Bures-sur-Yvette, France

[73] Assignee: Commissariat a l'Energie Atomique, Paris, France

[21] Appl. No.: 720,599

[22] Filed: Sept. 7, 1976

[51] Int. Cl.² .......................................... G01R 33/12
[52] U.S. Cl. ..................................................... 324/40
[58] Field of Search ................................... 324/37, 40

[56] References Cited

U.S. PATENT DOCUMENTS

| 3,229,198 | 1/1966 | Libby | 324/40 |
| 3,706,029 | 12/1972 | Wandling et al. | 324/40 |

Primary Examiner—Robert J. Corcoran
Attorney, Agent, or Firm—Cameron, Kerkam, Sutton, Stowell & Stowell

[57] ABSTRACT

A process of and apparatus for non-destructive eddy current testing involves the suppression of displayed lobes corresponding to fault parameters to be eliminated from the display. Elimination circuits are provided for operating on the measurement signal to remove the undesirable parameters from the signal by compensation of the effects produced by the parameters at different frequencies.

4 Claims, 6 Drawing Figures

PROCESS OF AND APPARATUS FOR NON-DESTRUCTIVE EDDY CURRENT TESTING INVOLVES THE SUPPRESSION OF DISPLAYED LOBES CORRESPONDING TO FAULT PARAMETERS TO BE ELIMINATED FROM THE DISPLAY

The present invention is concerned with a non-destructive testing process employing eddy currents and with an apparatus for carrying out this process. One application is in the testing of metallic workpieces, particularly tubular bundles intended for heat exchangers, condensers or steam generators.

It is known that testing by eddy currents consists of the study of variations of currents induced in a metal workpiece by the magnetic field of a coil carrying an alternating exciting current. Such currents produce, in turn, a field which opposes the inducing field, and consequently modifies the impedance of the excitation coil. This coil is disposed in a probe which moves along the workpiece to be tested. Any defect of the workpiece being examined, which is present at the level of the probe (change in dimension, variation of electric conductivity, cracks, etc.) modifies the flow or the intensity of the eddy currents and consequently the impedance of the coil.

The probe is usually made of two adjacent coils, energized in opposition and placed in the two adjacent branches of a measuring bridge. The passage of a fault in the field of the probe unbalances the bridge twice, first in one direction and then in the other. The voltage generated by the probe is amplified and, after analysis, may be represented on the screen of a cathode ray tube. This representation is effected by displaying the resistive (or real) component X of the voltage measured and the reactive (or imaginary) component Y. The complex voltage provided by the probe is thus represented by a point having the co-ordinates X and Y. When a fault passes into the field of the probe, the representative point describes a curve which is generally in the form of a figure of eight. Each fault can, therefore, be identified with reference to the phase of the lobe of the figure of eight (inclination relative to a reference axis) and by its amplitude.

Known techniques of testing by means of eddy currents, which utilize a single excitation frequency are not well suited to certain problems in which it is desired to test a workpiece which possesses either known or acceptable deformation, or discontinuities resulting for example from the presence of massive metallic bodies in the neighbourhood of the workpiece. This is the case, for example, with tubes intended for heat exchangers which are joined to a tubular plate, to a cross-piece or to anti-vibration bars. These discontinuities show themselves on the test apparatus by extremely important signals which could mask possible signals corresponding to faults being sought.

Techniques are known for eliminating parameters thought undesirable and for only retaining in the curve representing the variations of the signal produced by the probe the parts representative of the faults to be discovered. In this kind of technique multiple frequency excitation signals are used and the representative curve is successively rotated in such a way that the signals corresponding to the undesirable parameters disappear. Reference may be made, for example, to U.S. Pat. No. 3,706,029 issued on Dec. 12, 1972.

The present invention is concerned with a process and an apparatus in which the excitation is also effected at different frequencies and in which the contribution of one or more parameters is eliminated from the measurement signal. The originality of the invention resides in the manner in which this elimination is effected.

According to the invention use is made of the fact that the appearance of curves representing the excitation signal depends on the frequency of examination. It is consequently possible to eliminate the contribution of a parameter by judicious combination of the curves obtained at different frequencies, in such a way that the contribution of the undesirable parameter is compensated for by the contribution of the same parameter at a different frequency.

The invention is not restricted to the elimination of a single parameter; it also covers the case where $n-1$ parameters are eliminated with the assistance of an excitation signal composed of $n$ different frequencies.

More particularly, the invention is concerned with a process of non-destructive testing using eddy currents, of the kind in which:
- a probe is displaced in the proximity of a workpiece to be tested,
- said probe is supplied with an excitation current of $n$ different frequencies,
- the compounds of each of the $n$ frequencies of the signal produced by the probe are analysed, characterized in that:
- there are determined, for each component, its resistive part X in phase with the excitation current at the same frequency and its reactive part Y in quadrature,
- the parts $X_1$ and $Y_1$ of one component at a first frequency are modified so that they coincide, in the zone corresponding to a fault of a parameter to be eliminated, with the parts $X_2$ and $Y_2$ of a component at a second frequency,
- from the parts $X_1$ and $Y_1$ thus modified there are removed the parts $X_2$ and $Y_2$, which provides a new set of resistive and reactive parts X' and Y', permitting a representative curve to be obtained in which the contribution of the undesirable parameter has been eliminated,
- there is displayed on a plane the signal of the components X' and Y'.

The elimination of several parameters may be effected as just described, by combining judiciously the parts X and Y characterizing the components at two different frequencies, or by combining the parts X' and Y' resulting from a first elimination with the parts characterizing a component at another frequency.

The invention is also concerned with an apparatus which carries out the process which has been described and which is of the kind comprising:
- a probe disposed in the proximity of the workpiece to be tested, the probe and the workpiece being displaced one in relation to the other in the course of testing,
- means for supplying said probe with an excitation current resulting from the superposition of $n$ currents of excitation at $n$ different frequencies,
- means for extracting from the measuring signal provided by the probe the components of each of said $n$ frequencies, said means being constituted by $n$ analysing circuits giving, for each frequency, the resistive part X in phase with the excitation current at the same frequency and the reactive part Y in quadrature, means for representing a measurement signal, in a plane marked with two rectangular axes, one carrying the parts X and the other the parts Y of the components of the measurement signal, in such a way that, for each frequency, the point of said plane having the co-ordinates X and Y described during testing of the workpiece, a curve generally in the form of lobes, each lobe corresponding to a fault of a parameter of the workpiece to be tested, the apparatus according to the invention is characterized in that it further includes means for eliminating, in the representation of the measurement signal, the parts of the curve corresponding to faults affecting certain undesirable parameters, said means comprising as many elimination circuits as there are parameters to be eliminated, each elimination circuit comprising:

means for modifying the resistive and reactive parts $X_1$ and $Y_1$ of a component at a first frequency so that they coincide in the zone corresponding to a fault of the parameter to be eliminated, with the parts $X_2$ and $Y_2$ of a component at a second frequency, means for removing from the modified parts $X_1$ and $Y_1$ the parts $X_2$ and $Y_2$ which provides a new set of resistive and reactive parts $X'$ and $Y'$, applied thereafter to display means for the measurement signal, and which lead to a curve devoid of the lobe corresponding to the parameter to be eliminated.

In any case, the characteristics and advantages of the present invention will emerge better after the following description of embodiments given by way of explanation and in no way limiting the invention, with reference to the attached drawings, in which.

Figure 1:
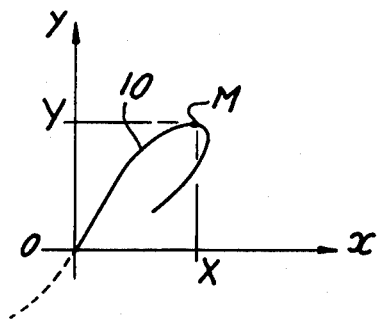
FIG. 1 shows the known principle of representing one component of the measurement voltage, by displaying, on a screen, a point the co-ordinates of which are equal respectively to the parts of the said component in phase and in phase quadrature with the excitation.

FIG. 1 illustrates the known principle of representing the measurement voltage issuing from a probe by eddy currents. The plane is marked with two rectangular axes $Ox$ - $Oy$, on which are carried the part X of the measurement signal in phase with the excitation signal and the part Y in phase quadrature with the excitation signal. In such a complex representation, the point M having the co-ordinates X and Y therefore represents, at any instant, the measurement voltage at one of the excitation frequencies, and the curve traced by this point illustrates the variations of the component at this frequency when the probe and the workpiece to be tested are displaced one in relation to the other. The curve described by the point M is usually in the form of a figure of eight, as is known. This curve carries the reference 10 and is only shown on this FIG. 1.

Figure 2:
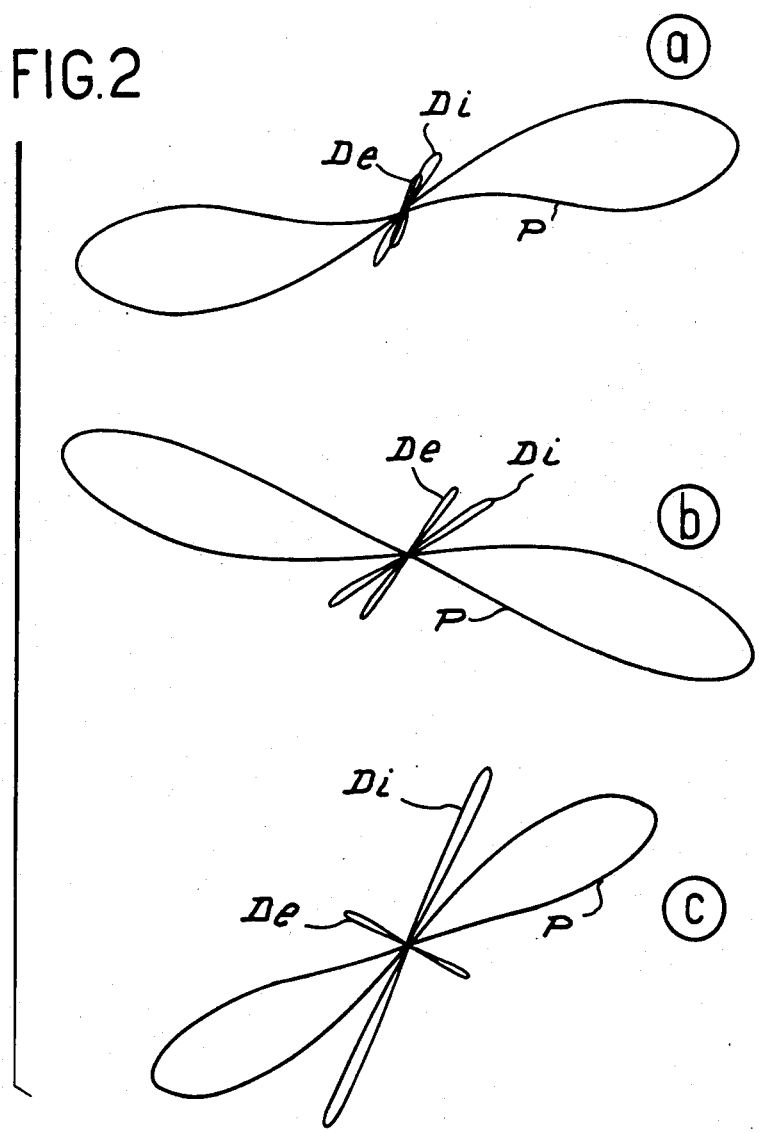
FIG. 2 illustrates different forms which the representative curve can take, for the same workpiece, when the excitation frequency is modified.

As is known, the amplitude and the inclination of the curve obtained depend on the examination frequency. This dependence is illustrated in FIG. 2, in the case where the workpiece is a tube of "Inconel" having the diameters 22.2 × 20.7 mm, in the interior of which the probe is displaced. For the purposes of the description it is assumed that this tube has an internal surface fault marked by the reference $D_i$, an external surface fault marked by the reference $D_e$ and an intermediate metallic plate fixed to the said tube, which introduces a discontinuity P. FIG. 2 represents the curves obtained for these three anomalies, at three different frequencies, respectively equal to 20 kHz, 100 kHz and 240 kHz.

For the frequency of 20 kHz, the internal and external faults have the same phase and are of small amplitude compared to the one which corresponds to the existence of the intermediate plate P. This is explained by the fact that at this low frequency the penetration of the magnetic field is important, which permits the field to reach the plate.

For the intermediate frequency of 100 kHz, the amplitude ratio is a little less important and the appearance of dephasing between the internal and external faults may be noted.

The frequency of 240 kHz corresponds to the case where dephasing between the internal and external faults is of the order of 90°. It is known, in fact, that there is a frequency for which dephasing between the faults situated on the inside of a tube and the faults situated on the outside of the tube takes this special value. On this point reference may be made, for example, to the report No. R4073 of the Commissariat a l'Energie Atomique, entitled "Contribution to the study of eddy currents and application to the multiparameter testing of tubes" by Michel Pigeon, published in October, 1970. In the present example, at this frequency of 240 kHz, the depth of penetration of the eddy currents is of the order of the thickness of the tube wall; there exists, therefore, only a weak field on the outside of the said tube, which explains the diminution of the amplitude of the signal corresponding to the existence of the intermediate plate. The ratio between the amplitudes of the internal and external faults is of the order of 0.4.

If it were required to eliminate entirely the fault corresponding to the plate P, it would be necessary then to continue to increase the frequency, but this would inevitably lead to the elimination of the external faults. This manner of proceeding would, therefore, not be judicious. By avoiding this disadvantage the invention permits just this elimination by a process the principle of which is illustrated schematically in FIG. 3.

In FIG. 3a, these faults correspond to a first frequency A and in FIG. 3b, to a frequency B. The frequency A is, for example, 100 kHz and the frequency B is 240 kHz. Each representation of a fault is affected by the indication A or B according to the frequency. Thus, the notation $\overline{D_eA}$ corresponds to the representation of the external fault for the frequency A.

FIG. 3c shows the faults obtained from FIG. 3a by a homothesis of ratio $k$, $k$ being chosen in such a way that the amplitude of the vector $kPA$ at the frequency A, corresponding to the plate P, becomes equal to the amplitude of the vector PB obtained at the frequency B. It goes without saying that the amplitudes of the vectors $D_eA$ and $D_iA$ for the frequency A undergo the same homothesis and become equal to $kD_eA$ and $kD_iA$. It is only by way of explanation that the co-ordinates X and Y had been supposed to be modified in the same ratio $k$; it would not be departing from the framework of the invention by multiplying the co-ordinates X by a first coefficient $k_x$ and the co-ordinates Y by a second coefficient $k_y$.

FIG. 3d shows the modification given to FIG. 3c when the said Figure is turned through an angle such that the vector kPA becomes parallel to the vector PB characterizing the same fault at the frequency B. In the effected rotation, the vectors $kD_eA$ and $kD_iA$ of course undergo the same rotation and become $kD'_eA$ and $kD'_iA$.

FIG. 3e shows the result obtained by subtracting the diagram of FIG. 3d from the diagram of FIG. 3b. As the vectors characterizing the discontinuity due to the presence of the plate have the same amplitude and the same phase in the diagrams 3b and 3d, these vectors disappear in the operation of subtraction, and there only subsist, in the diagram of FIG. 3e, the vectors characterizing the internal and external faults, that is to say a vector $\overrightarrow{D_iB}$-$\overrightarrow{kD'_iA}$ and $\overrightarrow{D_eB}$-$\overrightarrow{kD'_eA}$.

Figure 3:
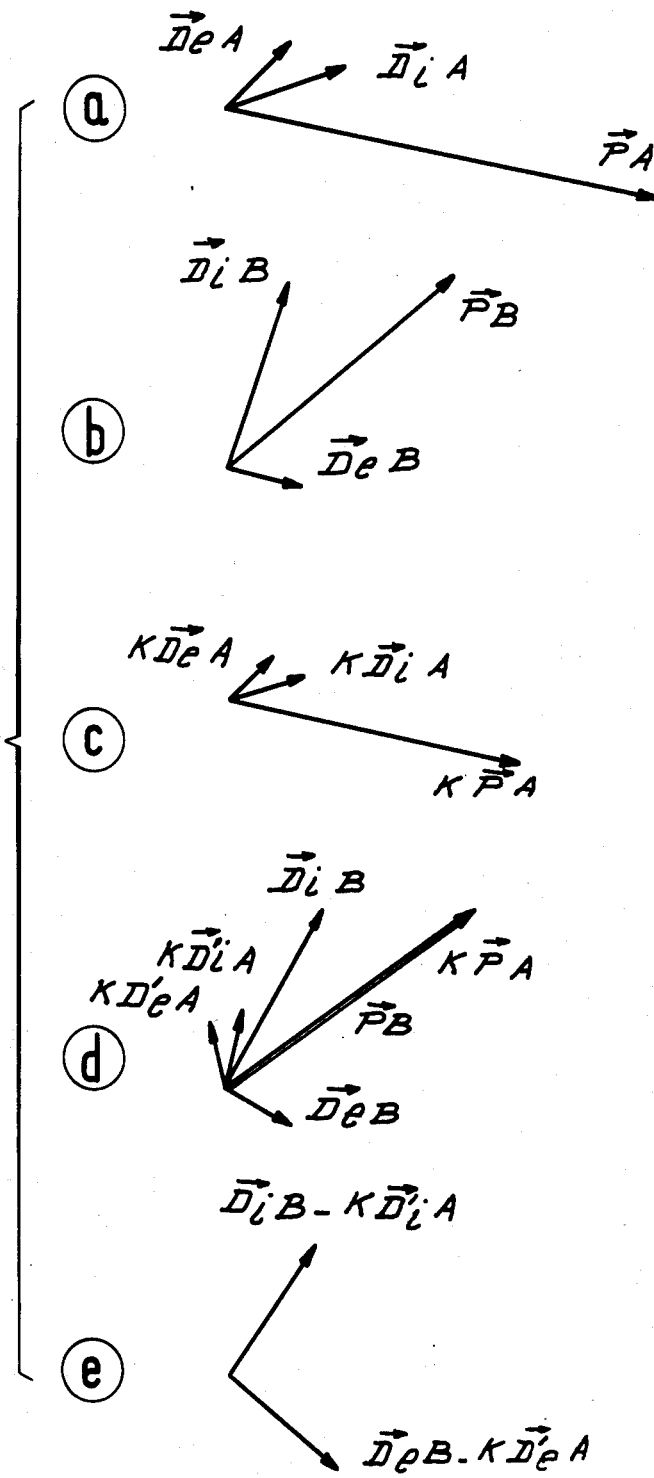
FIG. 3 illustrates the principle of elimination of a parameter, according to the invention, by compensation of the effects produced by this parameter at two different frequencies.

Of course the simplified representation used in FIG. 3 which assimilates one lobe of a vector does not necessarily imply that the said lobe only undergoes a homothetic rotation, because in the multiplication by $k_x$ and $k_y$, the lobe can be deformed if $k_x \neq k_y$.

By these transformations which characterize the process according to the invention, the curve representing the variations of the measurement signal has had removed the contribution made by the undesirable parameter P. This process is useful when the lobe corresponding to the undesirable parameter is well detached from the other lobes as is the case in FIG. 2, but, even more, it is useful when a fault which is to be detected is situated in the neighbourhood of the workpiece corresponding to the undesirable parameter; this is the case, for example, when a fault affecting the tube to be tested is situated in the neighbourhood of the plate. In this case, two lobes corresponding to the plate (an undesirable parameter to be eliminated) and to the fault (to be detected) are mixed and the second, if it is weak, can be swamped by the first. When the adjustment of the apparatus has been effected so that the lobe corresponding to the plate has been eliminated, according to the process of the invention, the lobe characterizing the fault then appears clearly and the fault can be analysed and identified.

The transformations characterizing the process of the invention are preferably effected on the resistive part X and reactive part Y of each component of the measurement signal. These parts can be obtained by effecting an analysis of the signal provided by the measuring probe, according to known methods. Reference may be made, for example, to the report already mentioned, and to the U.S. Pat. No. 3,229,198 of Jan. 11, 1966. By way of explanation, FIG. 4 shows the block diagram of a circuit for two frequencies, which allows the obtaining of these parts X and Y, for each of the two components of the measurement signal.

Figure 4:
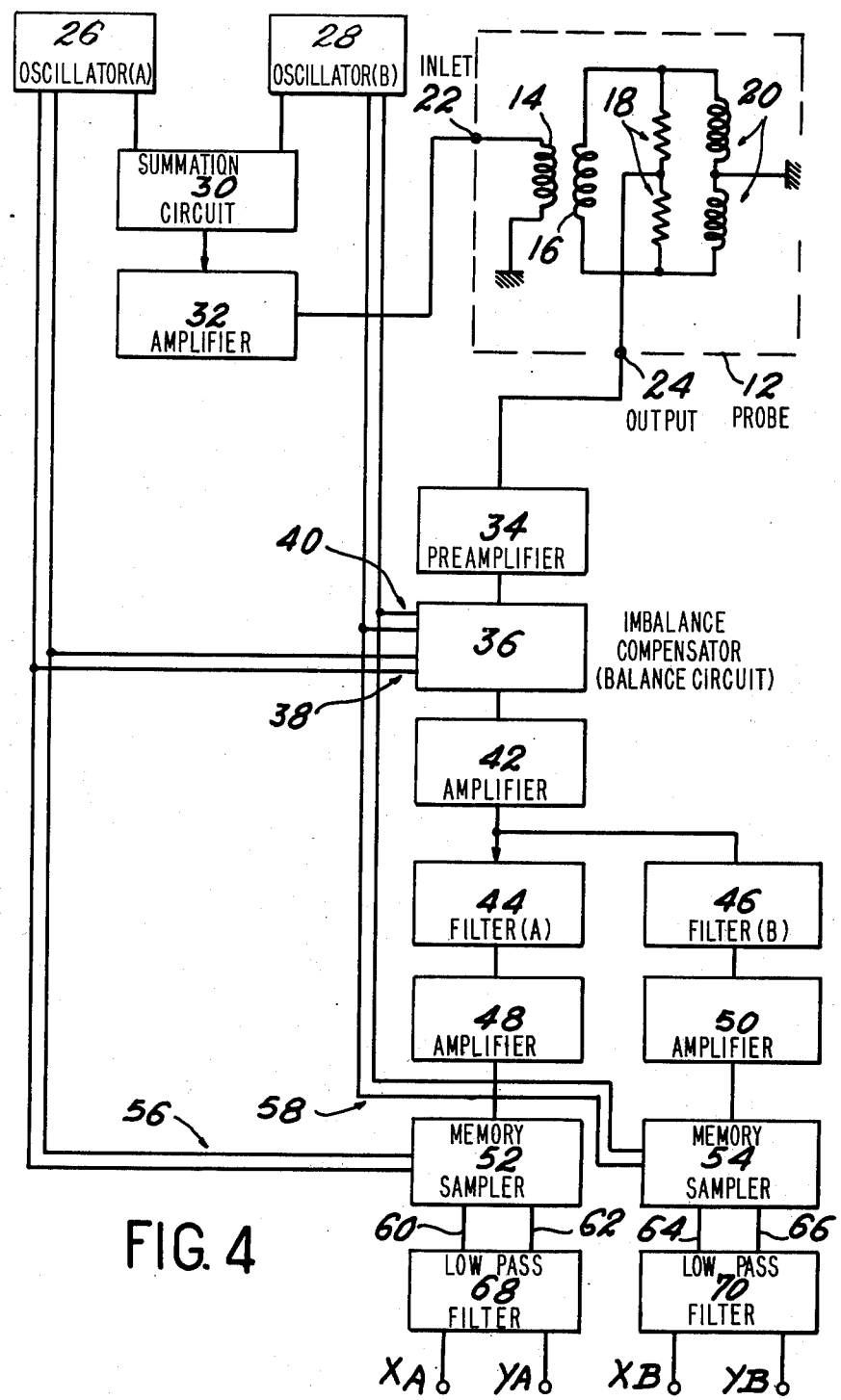
FIG. 4 represents a block diagram of a circuit for two frequencies, which allows the parts X and Y of each of the two components of the measurement signal to be obtained.

On FIG. 4, the probe carries the reference 12 and it comprises a first coil 14 coupled to a second coil 16, in a balanced bridge arrangement comprising two resistances 18 and two inductances 20. This probe has an input terminal 22 and an output terminal 24. The excitation means of such a probe include a first oscillator 26, providing a current at the frequency A and a second oscillator 28, providing a current of frequency B. The currents provided by these two oscillators are superimposed in a summation circuit 30, followed by an amplifier 32. The output of the said amplifier is connected to the input 22 of the probe.

The measurement signal provided by the probe is delivered by the output 24. This signal may be preamplified by the preamplification circuit 34, for example by a gain of 10 decibels, in order that the measurement signals may have a level sufficient for them to effect the balancing operation. These operations consist in compensating the imbalance of the construction of the probe and they are effected in a circuit referenced 36 and which is connected to the oscillators 26 and 28 respectively by the connexions 38 and 40 which carry the signals which are in phase and in phase quadrature with the currents provided by the oscillators. The measurement signal is amplified after balancing in an amplifying circuit 42, for example of a gain of 30 decibels, the said amplification being such that the signal does not undergo any saturation.

The measurement signal provided by the amplifier 42 comprises signals in two frequencies A and B which are separately filtered by means of a first band-pass filter 44, centered on the frequency A, and by a band-pass filter 46, centered on the frequency B. These filters are advantageously of strong slope, for example 24 decibels per octave. The signals thus filtered are then amplified by amplifying circuits 48 and 50 and then analysed by memory sampling circuits 52 and 54. These circuits receive by the connections 56 and 58, two reference signals at the frequencies A and B respectively in phase and in phase quadrature with the currents provided by the oscillators. These memory sampling circuits provide at their two output leads respectively 60-62 and 64-66 the parts X in phase and Y in phase quadrature with the excitation currents. These sampling circuits may be followed by low-pass filters 68 and 70, which permit elimination of residual base noise due to sampling. The entire circuit, therefore, delivers, definitively, the resistive and reactive parts $X_A$ and $Y_A$ for the components at the frequency A, and $X_B$ and $Y_B$ for the components at the frequency B. These signals X and Y are continuous voltages, which are variable with the displacement of the probe.

It goes without saying that this circuit is only described by way of example and that any other known means permitting the determination of the said resistive and reactive parts at each frequency may be associated with the elimination circuit such as will now be described with reference to FIG. 5.

Figure 5:
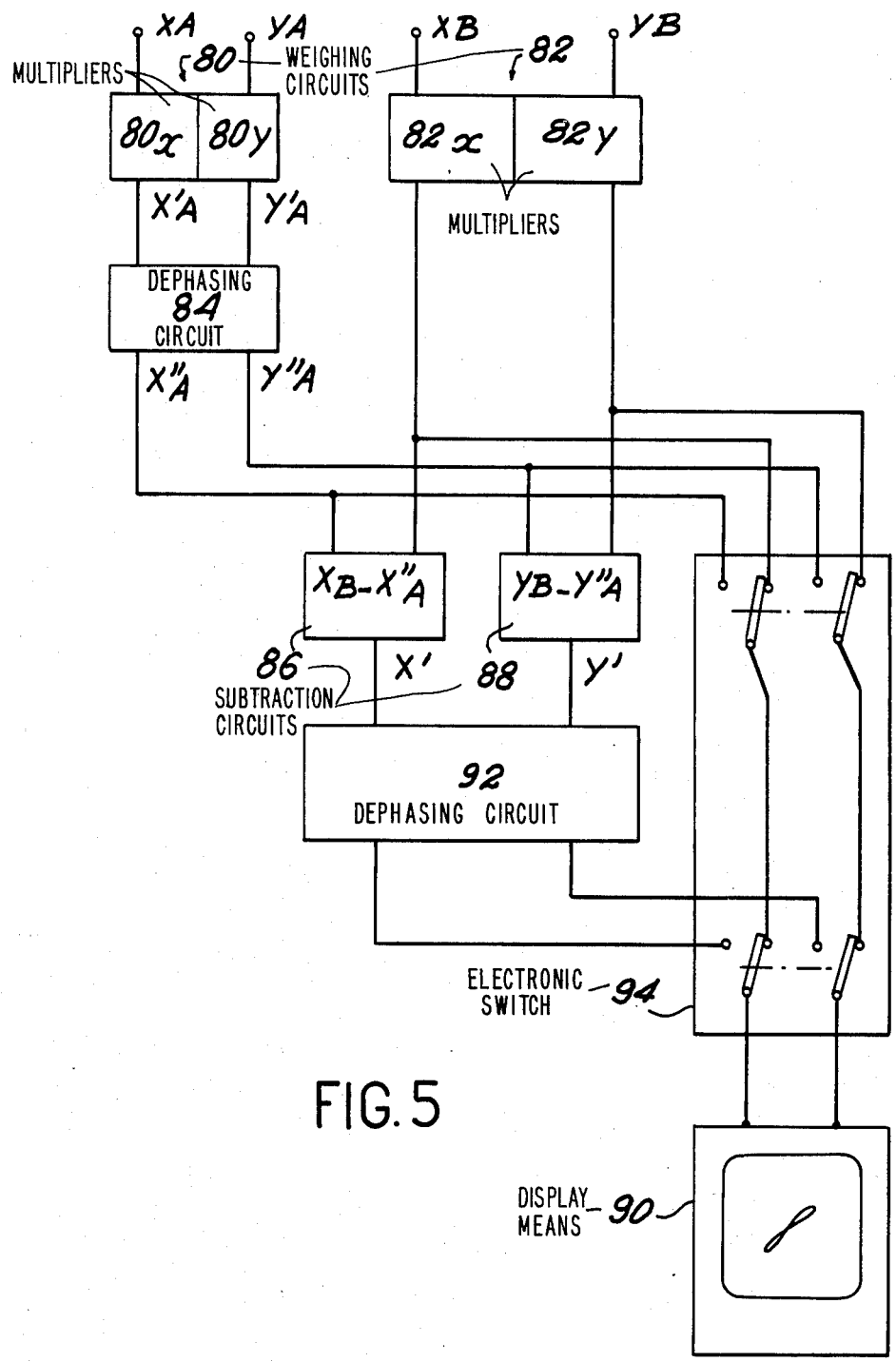
FIG. 5 represents a block diagram of a circuit permitting the elimination, according to the invention, of a parameter starting with two components of different frequencies.

The circuit of FIG. 5 is connected to the output of the analysis circuit represented in FIG. 4 and it, therefore, receives as its inputs the resistive and reactive parts $X_A$ and $Y_A$ corresponding to the frequency A and $X_B$ and $Y_B$ corresponding to the frequency B. This elimination circuit comprises a weighting circuit 80, on the path corresponding to the frequency A, formed by two multipliers 80x and 80y. This circuit multiplies the parts $X_A$ and $Y_A$ respectively by the coefficients $k_x$ and $k_y$, which are possibly equal, and supplies the parts $X'_A$ and $Y'_A$ which are such that the amplitude $\sqrt{X'^2_A + Y'^2_A}$ for the signal corresponding to the parameter to be eliminated as equal to the amplitude $\sqrt{X^2_B + Y^2_B}$ of the signal corresponding to the same parameter for the frequency B. In other words, the weighting circuit 80 effects that which corresponds to the operation illustrated in FIG. 3 in the case where $k_x = k_y$. This operation of weighting can also be effected simultaneously on the path B, if a second weighting circuit 82 is used on this path, comprising two multipliers 82x and 82y. The multiplier 80 is followed by a dephasing circuit 84, which modifies the parts $X'_A$ and $Y'_A$ and provides the new parts $X''_A$ and $Y''_A$ such that for the fault of the parameter to be eliminated, these new parts are equal to the corresponding parts $X_B$ and $Y_B$ at the frequency B. In other words, the dephasing circuit 84 effects the operation of rotation illustrated in FIG. 3d. Subtraction circuits 86 and 88 thereafter effect the difference between the resistive parts $X_B$ and $X''_A$ and $Y_B$ and $Y''_A$. At the output of the circuits 86 and 88 there are available two new resistive and reactive parts X' and Y' in which the undesirable parameter has been eliminated. These are the parts which are applied to the display means 90, possibly after passing through a dephasing circuit 92, which permits the orientation of the curves obtained on the screen of the means 90.

The display system 90 is advantageously associated with an electronic switch 94 which allows display on the screen the curve representing the component at the frequency A after the operations of weighting and rotation, which is obtained by applying to the means 90 the parts $X''_A$ and $Y''_A$ supplied by the dephaser 84. These switching means 94 also allow display on the screen of the curve corresponding to the frequency B. If the switch 94 comprises electronic cut-off, it is possible to show alternatively these two curves and so to regulate the weighting circuits 80 and dephasing circuits 84 so that after the operation of subtraction, the undesirable parameter will be conveniently eliminated. The switch 94 also permits the connection of the display means 90 to the output of the dephasing circuit 92 in order to show the curve obtained after elimination of the undesirable parameter. The circuit 84 allowing dephasing of the parts X and Y in relation to one another in such a way that the representative curve undergoes a rotation around the origin, is known to the expert in the art. Reference may be made on this subject to U.S. Pat. No. 3,706,029, already mentioned, where such circuits are described.

Of course the switching means 94 are only shown schematically in FIG. 5: they may be partially incorporated in the display means, particularly when these comprise a double beam cathode ray tube. These switching means may also be associated with a device for effacing the luminous spot on the screen when moving from one curve to the other. These means are well known and hence not shown, and may possibly be included in the display system 90.

Figure 6:
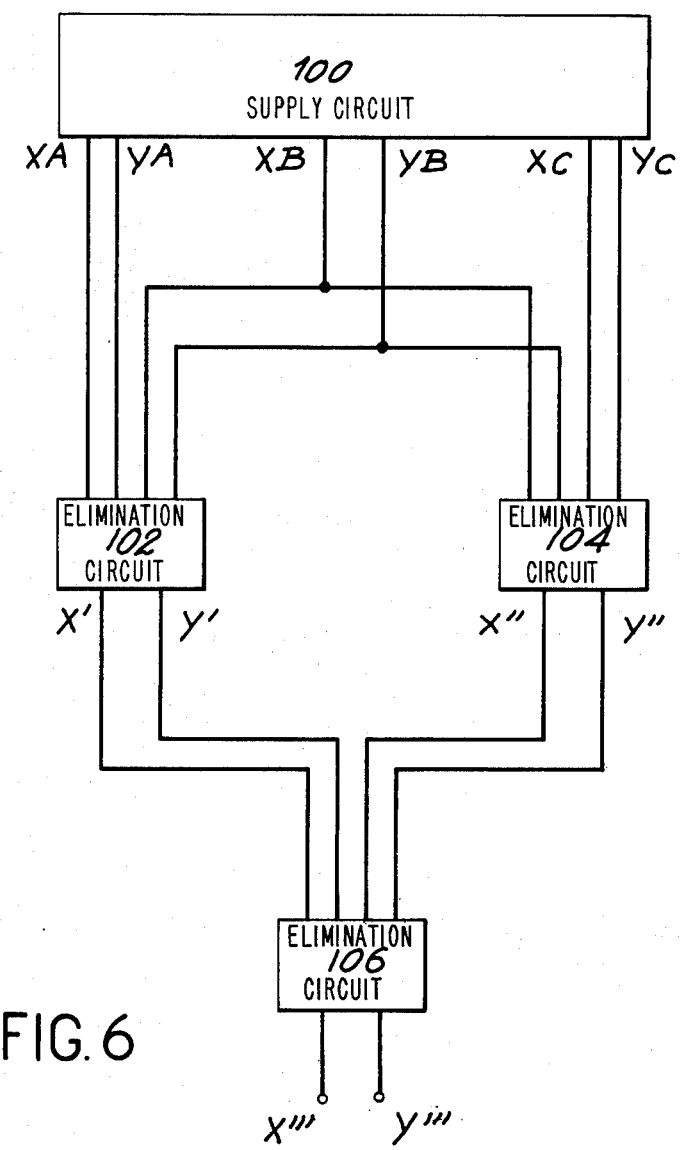
FIG. 6 represents a block diagram of a circuit permitting the elimination of two parameters between signals at three different frequencies.

The elimination of several parameters may be effected in a successive manner as shown schematically in FIG. 6.

In this figure there is shown a circuit allowing the elimination of two parameters between three signals at three different frequencies. The circuit 100 supplies the parts $X_A$ and $Y_A$ of one component at the frequency A, $X_B$ and $Y_B$ of a component at the frequency B and $X_C$ and $Y_C$ of a component at the frequency C. These components depend on three parameters $\alpha$, $\beta$ and $\gamma$. A first elimination circiut 102 receives the parts at frequencies A and B and supplies new parts X' Y' in which the parameter $\alpha$ has been eliminated. A second elimination circuit 104 receives the parts at frequencies B and C, and supplies new parts X'' and Y'' in which $\alpha$ has been eliminated. Each pair X', Y' and X'' and Y'' depends only on parameters $\beta$ and $\gamma$. A third elimination circuit 106 eliminates the parameters $\beta$ by using the parts X' and Y' on one hand, and X'' and Y'' on the other hand. This elimination circuit 106 provides the parts X''' and Y''' which only depend on the parameter $\gamma$. The parameters $\beta$ and $\alpha$ have, therefore, thus been eliminated.

I claim:

1. Process for non-destructive testing by eddy currents of the kind in which:

a probe is displaced in the proximity of the workpiece to be tested, said probe is supplied by an excitation current of n different frequencies, the components of each of the n frequencies in the measurement signal are analysed, the improvement comprising the steps of determining for each component, its resistive part X in phase with the excitation current at the same frequency, and its reactive part Y in quadrature, modifying the phase and amplitude of the determined parts $X_1$ and $Y_1$ for the signal at a first frequency so that the component of that signal due to a parameter to be eliminated is made to coincide in phase and amplitude with the parts $X_2$ and $Y_2$ for the signal at a second frequency due to the same parameter, subtracting the parts $X_2$ and $Y_2$ from the parts $X_1$ and $Y_1$ thus modified, which provides a new set of resistive and reactive parts X' and Y', permitting to be obtained a representative curve for which the contribution of the undesirable parameter has been eliminated, and displaying the signal of the components X' and Y' on a plane.

2. Process according to claim 1, the additional steps of having eliminated a first parameter in accordance with the process of claim 1, eliminating the same parameter in accordance with the process of claim 1 using the parts $X_2$ and $Y_2$ for the signal at the second frequency and the parts $X_3$ and $Y_3$ for the signal at a third frequency, thereby providing a new set of parts X'' and Y'', eliminating a second undesirable parameter by effecting the operations of claim 1 between the parts X' and Y' obtained after elimination of the first parameter, and the parts X'' and Y''.

3. Apparatus for non-destructive eddy current testing comprising:

a probe disposed in the proximity of a workpiece to be tested, the probe and the workpiece moving one in relation to the other in the course of testing, means for supplying said probe with an excitation current resulting from the superposition of n alternating excitation currents at n different frequencies, means for extracting from the measurement signal provided by the probe the components of each of said n frequencies, said means comprising n analysing circuits giving, for each frequency, the resistive part X in phase with the excitation current at the same frequency and the reactive part Y in quadrature, means for representing the measurement signal, in a plane marked by two axes at right angles to one another one carrying the parts X and the other the parts Y of the components of the measurement signal, in such a way that, for each frequency, the point of said plane having X and Y as co-ordinates, describes in the course of testing of said workpiece, a curve generally in the form of lobes, each lobe corresponding to a fault of a parameter of the workpiece under test.

the improvement comprising in addition means for eliminating, in the representation of the measurement signal, the parts of the curve corresponding to undesirable parameters, said means comprising:

means for modifying the phase and amplitude of parts $X_1$ and $Y_1$ for the signal at a first frequency so that the component of that signal due to a parameter to be eliminated, is made to coincide in phase and amplitude with the parts $X_2$ and $Y_2$ for the signal at a second frequency, due to the same parameter, means for subtracting the modified parts $X_1$ and $Y_1$ from the parts $X_2$ and $Y_2$, which provides a new set of resistive and reactive parts $X'$ and $Y'$, and means for thereafter applying parts $X'$ and $Y'$ to display means for the measurement signal and providing a curve devoid of the lobe corresponding to said eliminated parameter.

4. Apparatus according to claim 3, said eliminating means comprising:

a weighting circuit connected to the analysis circuit corresponding to the first frequency, said weighting circuit multiplying the parts $X_1$ and $Y_1$ supplied by said analysis circuit, by coefficients, and providing new co-ordinates $X'_1$ and $Y'_1$ such that the amplitude $\sqrt{X_1'^2 + Y_1'^2}$ for the signal at the first frequency corresponding to the parameter to be eliminated is equal to the amplitude $\sqrt{X_2^2 + Y_2^2}$ of the same signal for the parameter, at the second frequency, a dephaser, connected at the output of the weighting means, modifying the parts $X_1'$ and $Y_1'$ supplied by the weighting means and supplying new parts $X_1''$ and $Y_1''$ respectively equal in phase to the parts $X_2$ and $Y_2$ corresponding to the second frequency, a subtractor receiving the set of parts $X_1''$ and $Y_1''$ corresponding to the first frequency and outputs of the dephaser and the set of parts $X_2$ and $Y_2$ corresponding to the second frequency and outputs of the analysis circuit at the second frequency, and effecting the difference between said parts, which provides two new parts $X'$ and $Y'$ in which said parameter has been eliminated.

* * * * *